United States Patent [19]

Oviatt

[11] Patent Number: 5,699,574

[45] Date of Patent: Dec. 23, 1997

[54] EXTENDIBLE APPLICATOR

[76] Inventor: Jeffrey J. Oviatt, 5120 E. Orchard Ave., Nampa, Id. 83687

[21] Appl. No.: 643,506

[22] Filed: May 6, 1996

[51] Int. Cl.⁶ .................................................. A47K 7/02
[52] U.S. Cl. .................. 15/210.1; 15/144.4; 15/184; 15/244.1; 15/144.3; 132/320
[58] Field of Search ....................... 15/144.3, 144.4, 15/184, 209.1, 210.1, 104.94, 244.1; 132/317, 320; 401/6; D28/7

[56] References Cited

U.S. PATENT DOCUMENTS

| 255,851 | 4/1882 | Gross et al. | 15/184 X |
|---|---|---|---|
| D. 299,558 | 1/1989 | Robison | D28/7 |
| D. 323,568 | 1/1992 | Hackler | D28/63 |
| 1,703,257 | 2/1929 | Bengel | 15/209.1 |
| 1,973,768 | 9/1934 | Knapp | 15/144.3 X |
| 2,206,153 | 7/1940 | Berggruen | 15/210.1 |
| 4,135,274 | 1/1979 | Freeman | 15/144.4 X |
| 4,308,879 | 1/1982 | Thornbloom | 132/317 |
| 4,396,028 | 8/1983 | Waggoner | 15/144.4 |
| 4,483,356 | 11/1984 | Kales | 15/210.1 X |
| 4,527,574 | 7/1985 | Manfredi | . |
| 4,961,661 | 10/1990 | Sutton et al. | 401/6 |
| 5,044,386 | 9/1991 | Nelson | 132/309 |
| 5,117,848 | 6/1992 | Huang | 132/308 |
| 5,360,111 | 11/1994 | Arispe | 206/361 |
| 5,400,457 | 3/1995 | Ridgley | 15/167.1 |
| 5,493,749 | 2/1996 | Zayas | 15/244.1 X |

FOREIGN PATENT DOCUMENTS

| 2155774 | 10/1985 | United Kingdom | 132/320 |
|---|---|---|---|

*Primary Examiner*—Mark Spisich
*Attorney, Agent, or Firm*—Joseph W. Holland

[57] ABSTRACT

An applicator having an extendible handle including a lower handle section having a tubular configuration and an upper handle section being extendible from the lower tubular handle section with the upper handle section having a pad or attached thereto for application of oils, lotions and the like.

9 Claims, 2 Drawing Sheets

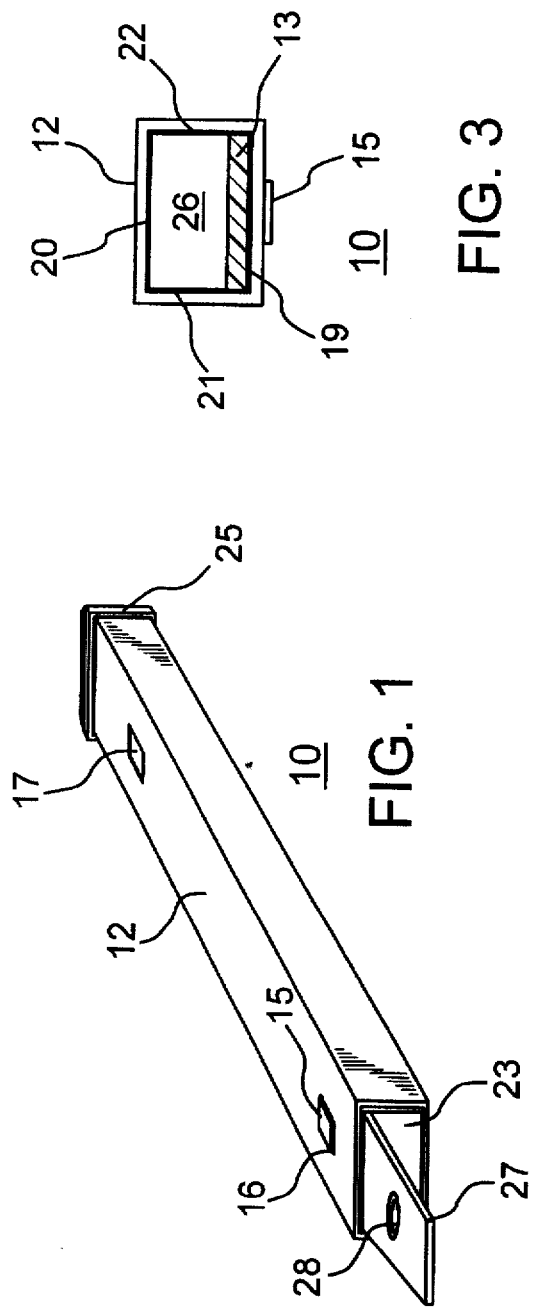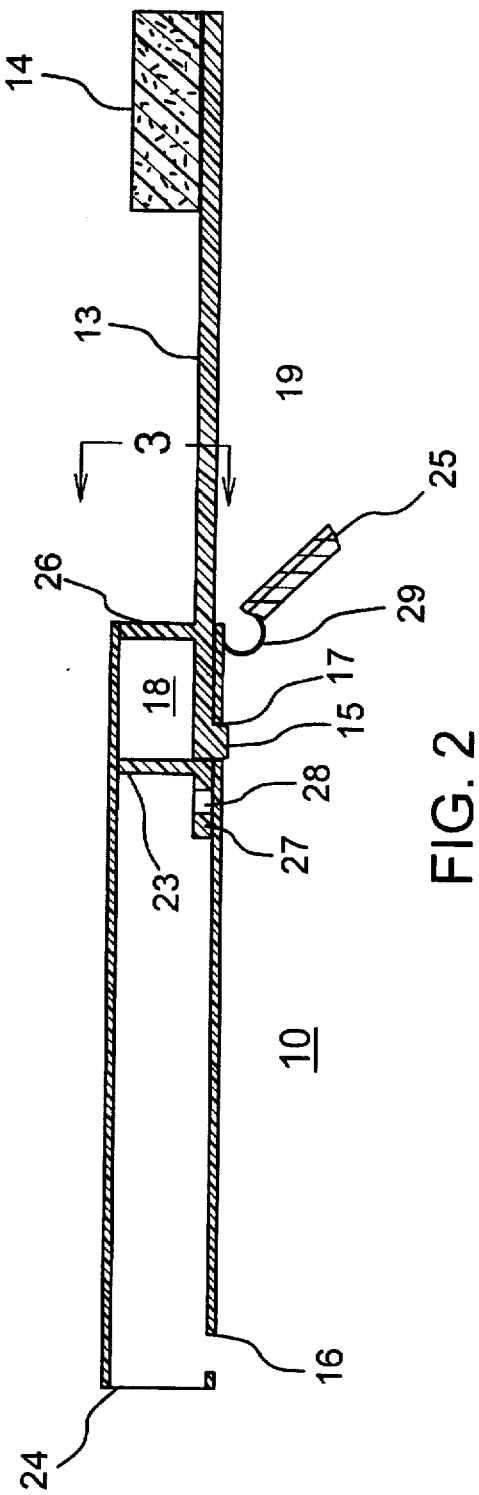

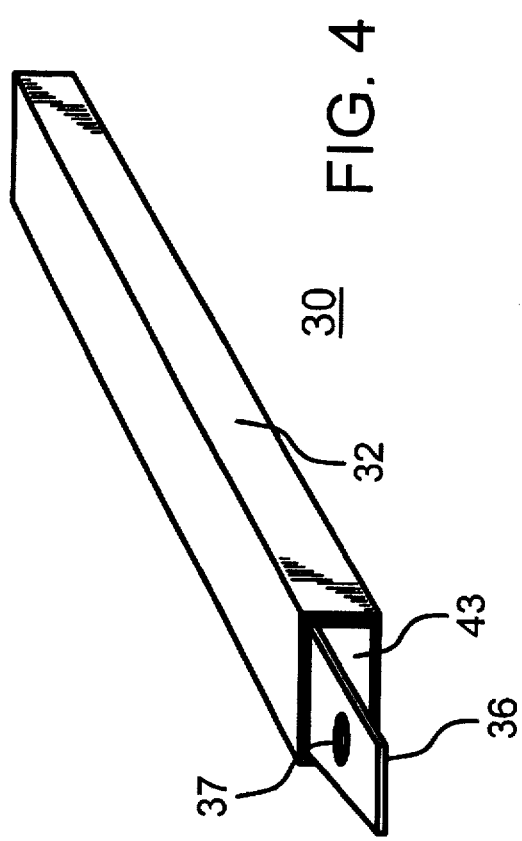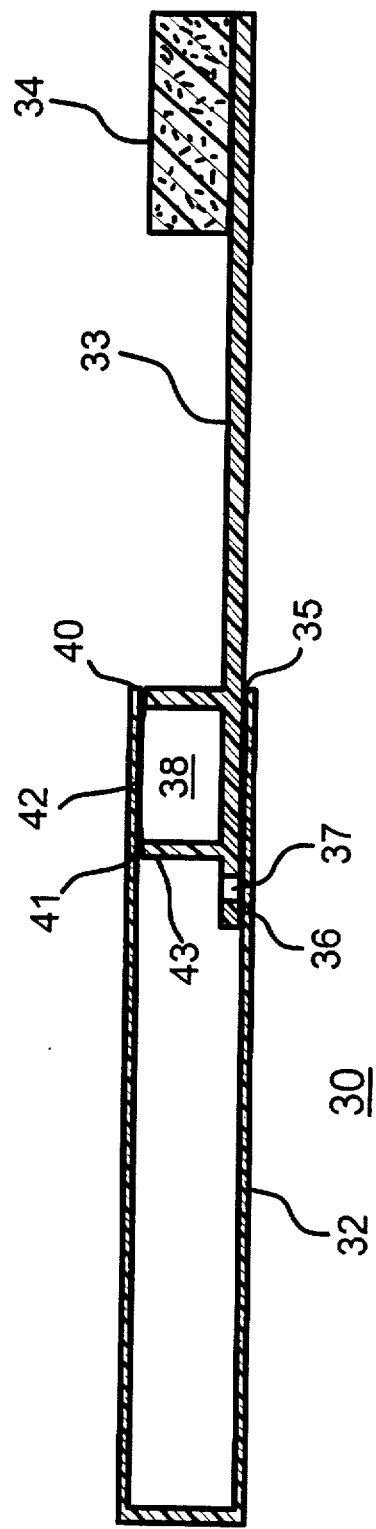

EXTENDIBLE APPLICATOR

BACKGROUND OF THE INVENTION

1. Technical Field

This application relates to applicators for viscous liquids and solutions and more specifically to an applicator which is extendible and fully self contained having a storage case integral to its construction.

2. Background

For the greatest part of the population, reaching the center of the back for applying viscous liquids and solutions such as sun screens, sun tan lotion or other body lotions or oils, presents a near impossibility. Nevertheless, with the public's increasing awareness relative to the potential harm of ultraviolet radiation from the sun, the need to uniformly apply sun screening lotions becomes more important to users.

In addition, elderly persons and those with certain physical handicaps, limitations or restrictions, may find it useful to have available a device which facilitates the treatment of the skin on parts of their bodies which may be otherwise difficult to reach with liquid or viscous solutions, lotions, oils and other solutions. For instance, many elderly persons have lost a degree of flexibility which allows them to treat their feet, ankles or lower legs with such substances. Similarly, these persons may find advantage in an extendible device having a pumice stone or other mild abrasive for attached to the end for treating corns, calluses and such.

Arispe, U.S. Pat. No. 5,360,111, Compact Lotion Applicator, discloses an applicator for tanning lotions having a telescoping handle which removably attaches to an applicator base. The handle telescopes out for use and collapses, together with the detachable applicator base, fits within a closeable compact for carrying and storage.

Yet another applicator is shown in Robison, Design Pat. No. D 299,558, Combined Body Lotion Applicator and Cover Therefore, which shows an applicator having a handle rigidly attached thereto. Robison also shows a detachable cover for the applicator pad in its design.

Similarly, Hackler, Design Pat. No. D 323,568, Combined Dispensing Applicator and Cover Therefore, shows an applicator having a handle rigidly attached thereto with a detachable cover for the applicator pad in its design.

In the case of Arispe, the handle and applicator are completely detachable from the compact, and there is a distinct possibility of misplacing the case while the applicator is being used. Similarly, because the applicator base is removably detachable from the handle, it too may be misplaced. Similar problems may arise with the devices depicted in Hackler and Robison, where the cover for the applicator pad is completely detachable from the applicator itself. Also in the cases of Hackler and Robison, the depicted designs feature rigid, non-collapsible handles which does not contribute to the compactability or portability of the implement.

It would be desirable to have an extendible applicator which incorporates the features of compactability, portability as well as the feature of enabling the user to enclose the apparatus when not in use so that the applicator pad is not fouled by foreign substances and residue lotions or oils on the pad do not come in contact with surfaces upon which the presence of these lotions or oils is unwanted or undesirable.

Several fully enclosing designs are found in art relating to toothbrushes. For instance, Ridgley, U.S. Pat. No. 5,400, 457, Collapsible Toothbrush, shows a toothbrush having a collapsible or telescoping handle with a head which folds or pivots at the top of the handle. Huang, U.S. Pat. No. 5,117,848, Combined Toothbrush and Pen-Shaped Casing, discloses a combined toothbrush with a pen-shaped casing, having a toothbrush removably confined inside the pen-shaped casing, the toothbrush being removable from the pen-shaped casing and inserted in an opening in one end of the pen.

Similarly, Nelson, U.S. Pat. No. 5,044,386, Portable Dental Care Unit, discloses a portable toothbrush having a base which includes means for selectively attaching the base to complementary means on the lower end of the toothbrush to form a handle for the toothbrush, the toothbrush being removable from the handle and the toothbrush having a closure means for enclosing at least the bristle portion of the toothbrush.

Finally, Manfredi, U.S. Pat. No. 4,527,574, Portable Dental Kit, discloses a toothbrush having a handle with a toothbrush removably attachable to the handle. Manfredi also claims a removable cover means for the toothbrush.

It would be desirable to have an extendible applicator for viscous liquids or for attachment of a pumice stone other mild abrasive for treating corns, calluses and the like, allowing the user to more easily apply viscous solutions or otherwise treat the skin on their back or other parts of their body which may be difficult to reach. It would also be desirable to have an extendible applicator which would be fully self-contained, having a cover or enclosure means for the applicator pad so that when the applicator is not in use, the pad may be protected from soiling or from contaminating surfaces which it may come in contact with. Additionally, the applicator may provide means for locking or otherwise securing the applicator in either its extended configuration or its retracted position. The applicator may provide means for easily changing a worn or soiled pad with new pad or other skin treating implement such as an abrasive. Finally, it would be desirable to provide means for hanging the applicator or attaching the applicator to a leash or wrist strap.

Therefore, a first object of the present invention is to provide an extendible applicator having an extendible handle including at least a lower tubular handle section and an upper handle section being extendible from the lower tubular handle section with the upper handle section of the having a skin treating means attached thereto.

Another object of the present invention is to provide a extendible applicator having an extendible handle including a tubular lower tubular handle section configured such that when the extendible applicator is not in use, the upper handle section may be enclosed within the lower tubular handle section.

Another object of the present invention is to provide integral closure means between the lower tubular handle section of the extendible handle and the upper handle section of the extendible handle configured so that when the applicator is not in use or is in the retracted position, the applicator pad or other skin treatment pad is enclosed and not subject to the environment.

Another object of the present invention is to provide a securing means between the lower tubular handle section of the extendible handle and the extendible upper handle section configured so that when the applicator is in either the extended or the enclosed position, the applicator is secure in such position until such time as the user desires to change the configuration.

SUMMARY OF THE INVENTION

According to the present invention, these and other objects are achieved by a extendible applicator having an extendible handle including a lower section being formed of a tubular member having a cavity therein projecting through the first or upper end of the lower section, through the length of the lower section and through the second end of the lower section, and an upper handle section being extendible from within the lower tubular handle section with the upper handle section having a skin treatment means attached thereto.

In the first or preferred embodiment of the invention, the upper handle section is both extendible and retractable within the lower tubular handle section. In the retracted position, a locking spring tab having a given outer perimeter shape and size, located on the upper handle section locks into a receiver of a corresponding and slightly larger inner perimeter shape and size located near the bottom end in the lower tubular handle section. Similarly, in the extended position, the locking spring tab located on the upper handle section locks into a receiver of a corresponding and slightly larger inner perimeter shape and size located near the top end of the lower tubular handle section. In the retracted position, a neck portion of the lower end of the upper handle section is positioned snugly within lower tubular handle section and closes off the second or lower end of the lower tubular handle section.

In the preferred embodiment of the invention, a cap covers the opening of the first or upper end of the lower tubular handle section when the applicator is not in use, the cap being attached to the lower tubular handle section in such a manner that when the applicator is in use, the cap remains attached to the lower tubular handle section, simply swinging or pivoting out of the way of the extendible upper handle section.

In a second embodiment of the invention, the lower handle section is formed of a tubular member having a cavity projecting through the first or upper end, through the length of the lower section, the second or lower end of the lower section being closed off, and an upper handle section being extendible from the lower tubular handle section, the upper handle section, having the applicator pad or other skin treatment means thereon, being slideably engageable within the lower tubular handle section when the applicator is not in use. In this configuration, the outer perimeter shape and size of the neck of the lower end of the upper handle section achieving a tight sliding fit within the opening in the top end of the lower tubular handle section, the opening having a corresponding and slightly larger inner perimeter shape and size than the outer perimeter shape and size of the neck of the lower end.

In order to use the applicator, the upper handle section is withdrawn from the lower tubular handle section and reversed, inserting the neck of the lower end of the upper handle section into the opening in the top end of the lower tubular handle section, once again securing, by means of the tight sliding fit, the upper handle section in an extended position for use as an applicator. Alternatively, this embodiment may employ a locking spring tab located on the upper handle section which locks into a receiver of a corresponding and slightly larger inner perimeter shape and size located near the top end of the lower tubular handle section. It is also possible that the neck of the lower end of the upper handle section may be configured to provide a storage cavity for storage of replacement pads, solution containers or the like.

As can be seen, either of the described embodiments of the extendible applicator include an upper handle section which is slideably engageable within a lower tubular handle section. Similarly, each of the described embodiments of the extendible applicator provide means for enclosing the upper handle section of the handle within the lower tubular handle section of the handle when the applicator is not in use.

Each of the described embodiments of the present invention provide securing means between the lower tubular handle section and the upper handle section configured to selectively prevent the upper handle section from sliding in relation to the lower tubular handle section. Similarly, each of the described embodiments of the invention is configured having an applicator pad or other skin treatment means located at the upper end of the extendible upper handle section.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

FIG. 1 is a perspective representation of a first embodiment of the extendible applicator;

FIG. 2 is a sectional representation of a first embodiment of the extendible applicator;

FIG. 3 is a sectional end view representation of a first embodiment of the extendible applicator;

FIG. 4 is a perspective representation of a second embodiment of the extendible applicator;

FIG. 5 is a sectional representation of a second embodiment of the extendible applicator; and

DETAILED DESCRIPTION OF THE INVENTION

Referring now to FIGS. 1 through 5, the features of the extendible applicator are more fully appreciated and understood. Referring to FIGS. 1 through 3, a first embodiment of extendible applicator 10 is shown to advantage. Extendible applicator 10 includes lower tubular handle section 12 and upper handle section 13. In the preferred embodiment of the invention, lower tubular handle section 12 is formed of a tubular plastic molding, lower tubular handle section 12 having a cavity projecting therethrough along its longitudinal axis. Upper handle section 13 is extendible from lower tubular handle section 12. Applicator pad 14 is attached at the uppermost end of upper handle section 13. In the preferred embodiment of the invention, applicator pad 14 is removably attached to facilitate replacement in the event that the pad becomes worn or soiled.

Referring to FIGS. 1 and 3, in this first embodiment of extendible applicator 10, upper handle section 13 is both extendible and retractable within lower tubular handle section 12. In the retracted position shown in FIG. 1, locking spring tab 15 locks into first spring tab receiver 16 located near the lower end of lower tubular handle section 12. Similarly, in the extended position shown in FIG. 2, locking spring tab 15 locks into second spring tab receiver 17 located near the upper end of lower tubular handle section 12. Locking spring tab 15 has a given outer perimeter shape and size and both first spring tab receiver 16 and second spring tab receiver 17 are configured such as to have a inner perimeter shape and size which corresponds to and is slightly larger than the given outer perimeter shape and size of locking spring tab 15.

Referring to FIG. 3, upper handle section neck 18 is shown to advantage. As can be seen, upper handle section neck 18 has a given outer perimeter shape and size and the inside perimeter of lower tubular handle section 12 is configured so as to have an inner perimeter shape and size which corresponds to and is slightly larger than the given outer perimeter shape and size of upper handle section neck 18. In this manner, a sliding fit and contact is maintained between the outer perimeter of upper handle section neck 18 and the inner perimeter of lower tubular handle section 12.

Specifically, backside 19 of upper, handle section neck 18 and topside 20 of upper handle section neck 18 are in sliding contact with the bottom inside surface and the upper inside surface of upper handle section neck 18 respectively. Similarly, upper handle section neck 18 is configured so that a sliding contact is maintained between first side surface 21 and second side surface 22 of upper handle section neck 18 and the first and second inside surfaces of lower tubular handle section 12 respectively. In this manner, upper handle section 13 is held securely within lower tubular handle section 12 while still being both extendible and retractable within lower tubular handle section 12.

In the preferred embodiment of the invention, enclosure of applicator pad 14 within lower tubular handle section 12 when applicator 10 is in a retracted configuration, as shown in FIG. 1, is achieved by bottom end 23 of upper handle section neck 18 effectively closing off hole 24 located at the end of lower tubular handle section 12. Similarly, cap 25 covers upper opening 26 of lower tubular handle section 12. Cap 27 is hingedly attached to lower tubular handle section 12. Alternatively, lower tubular handle section 12 may be molded having a closed or blind lower end.

As can be seen in FIG. 1, extendible applicator 10 includes attachment means 27 having hole 28 shown projecting from the lower end of upper handle section 13.

When a user desires to convert extendible applicator 10 from a retracted configuration, as shown in FIG. 1, to an extended configuration, as shown in FIG. 2, cap 25 is removed from upper opening 26 allowing the user to slideably extend upper handle section 13 out of lower tubular handle section 12. Because cap 25 is hingedly attached to lower tubular handle section 12, when extendible applicator 10 is in use, cap 25 remains attached to lower tubular handle section 12, simply swinging or pivoting out of the way.

Referring to FIGS. 4 and 5, a second embodiment of extendible applicator 30 is shown to advantage. Extendible applicator 30 includes lower tubular handle section 32 and upper handle section 33. In the preferred embodiment of the invention, lower tubular handle section 32 is formed of a tubular plastic molding, lower tubular handle section 32 molded having a closed or blind lower end and a cavity projecting into lower tubular handle section 32 from its upper end along its longitudinal axis. Upper handle section 33 is extendible from lower tubular handle section 32. Applicator pad 34 is attached at the uppermost end of upper handle section 33. In the preferred embodiment of the invention, applicator pad 34 is removably attached to facilitate replacement in the event that the pad becomes worn or soiled.

In this second embodiment of the invention, upper handle section 33 slideably engages within lower tubular handle section 32 when the applicator is not in use. The outer perimeter shape and size of upper handle section neck 38 of the lower end of upper handle section 33, at its greatest dimension, achieves a tight sliding fit within opening 35 located in the top end of lower tubular handle section 32.

More specifically, in the preferred embodiment, upper handle section neck 38 is configured as a double taper, having first inclined portion 40, second inclined portion 41 and flat 42 located in between, although it is recognized that other configurations may be employed to achieve the required tight sliding fit. Opening 35 has an inner perimeter having a corresponding and slightly larger shape and size than the outer perimeter shape and size of upper handle section neck 38 at flat 42. Alternatively, extendible applicator 30 may employ a locking spring tab mechanism as shown in the preferred embodiment which locks into a spring tab receiver located near the upper end of lower tubular handle section 32. Both the locking spring tab mechanism and the spring tab receiver would be configured so that in either the enclosed configuration or the extended configuration, the spring tab would engage the spring tab receiver.

In order to use extendible applicator 30, upper handle section 33 is withdrawn entirely from lower tubular handle section 32, reversed and upper handle section neck 38 located at the lower end of upper handle section 33 is inserted into opening 35.

Enclosure of applicator pad 34 within lower tubular handle section 32 is achieved by the fact that the outer perimeter shape and size of upper handle section neck 38 of the lower end of upper handle section 33, at its greatest dimension, which in the preferred embodiment, is located at flat 42, achieves a tight sliding fit within opening 35 located in the top end of lower tubular handle section 32 with backside 43 of upper handle section neck 38 fitting within and effectively closing off opening 35.

As can be seen in FIG. 4, extendible applicator 30 includes attachment means 36 shown projecting from the lower end of upper handle section 33.

While there is shown and described the preferred embodiment of the invention, it is to be distinctly understood that this invention is not limited thereto but may be variously embodied to practice within the scope of the following claims.

I claim:

1. An extendible applicator device comprising:
    a lower tubular handle section, having an upper end and a lower end, the lower tubular handle section having a longitudinal axis;
    an upper handle section having first and second ends, the upper handle section being slideably engageable within the lower tubular handle section;
    securing means between the lower tubular handle section and the upper handle section configured to selectively prevent the upper handle section from sliding in relation to the lower tubular handle section, the securing means including the upper handle section configured having a locking spring tab located thereon, the locking spring tab having a predetermined outer perimeter shape and size, and the lower tubular handle section configured having a locking spring tab receiver therein, the locking spring tab receiver configured having a predetermined inner perimeter shape and size which corresponds to and is slightly larger than the predetermined outer perimeter shape and size of the locking spring tab; and
    an applicator pad attached at the second end of upper handle section.

2. The extendible applicator device of claim 1 wherein the upper handle section is both extendible and retractable within the lower tubular handle section.

3. The extendible applicator device of claim 1 further comprising means for enclosing the applicator pad attached to the upper handle section within the lower tubular handle section when the applicator is not in use.

4. The extendable applicator device of claim 3 wherein the means for enclosing the applicator pad attached at the second end of upper handle section within the lower tubular handle section further comprises:

a bottom end of an upper handle section neck located at the first end of the upper handle section having a given outer perimeter shape and size which corresponds to and is slightly smaller in overall dimension than the inner perimeter shape and size of the lower tubular handle section configured to close off the lower end of lower tubular handle section when the extendible applicator device is in an enclosed configuration; and a cap for covering the upper end of lower tubular handle section.

5. The extendable applicator device of claim 3 wherein the means for enclosing the applicator pad attached at the second end of upper handle section within the lower tubular handle section further comprises:

a closed bottom end of the lower tubular handle section; and a cap for covering the upper end of lower tubular handle section.

6. The extendable applicator device of claims 4 or 5 wherein the cap for covering the upper end of lower tubular handle section further comprises means for hingedly attaching the cap to the lower tubular handle section.

7. The extendible applicator device of claim 1 wherein the securing means between the lower tubular handle section and the upper handle section configured to selectively prevent the upper handle section from sliding in relation to the lower tubular handle section further comprising the lower tubular handle section configured having a pair of locking spring tab receivers therein, each locking spring tab receiver configured having a predetermined inner perimeter shape and size which corresponds to and is slightly larger than the predetermined outer perimeter shape and size of locking spring tab, the first locking spring tab receiver being located near the lower end of the lower tubular handle section for securing the upper handle section in locked relation to the lower tubular handle section when the extendible applicator is in a retracted configuration, and the second locking spring tab receiver being located near the upper end of the lower tubular handle section for securing the upper handle section in locked relation to the lower tubular handle section when the extendible applicator is in an extended configuration.

8. The extendible applicator device of claim 1 wherein the securing means between the lower tubular handle section and the upper handle section configured to selectively prevent the upper handle section from sliding in relation to the lower tubular handle section further comprises the upper handle section configured to allow a tight sliding fit between the upper handle section outer perimeter and the lower tubular handle section inner perimeter.

9. The extendible applicator device of claim 1 wherein the upper handle section further comprises an upper handle section neck located at the first end of the upper handle section, the upper handle section neck configured having a given outer perimeter shape and size which corresponds to and is slightly smaller in overall dimension than the inner perimeter shape and size of the lower tubular handle section for allowing a tight sliding fit between the upper handle section and the lower tubular handle section.

* * * * *